United States Patent
Bar-Tal et al.

(10) Patent No.: US 10,588,543 B2
(45) Date of Patent: Mar. 17, 2020

(54) POSITION SENSING USING ELECTRIC DIPOLE FIELDS

(71) Applicant: BIOSENSE WEBSTER (ISRAEL), LTD., Yokneam (IL)

(72) Inventors: Meir Bar-Tal, Haifa (IL); Daniel Osadchy, Haifa (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 1051 days.

(21) Appl. No.: 13/869,301

(22) Filed: Apr. 24, 2013

(65) Prior Publication Data

US 2013/0317334 A1 Nov. 28, 2013

Related U.S. Application Data

(60) Provisional application No. 61/650,631, filed on May 23, 2012.

(51) Int. Cl.
*A61B 5/00* (2006.01)
*A61B 5/06* (2006.01)
(Continued)

(52) U.S. Cl.
CPC .......... *A61B 5/068* (2013.01); *A61B 5/0538* (2013.01); *A61B 5/061* (2013.01); *A61B 5/062* (2013.01);
(Continued)

(58) Field of Classification Search
CPC ....... A61B 5/068; A61B 5/0538; A61B 5/053; A61B 5/6852; A61M 2025/0166; A61M 2025/109
(Continued)

(56) References Cited

U.S. PATENT DOCUMENTS 4,630,611 A * 12/1986 King ............... A61B 5/076 600/377
4,722,353 A * 2/1988 Sluetz ............. A61N 1/0565 607/128
(Continued)

FOREIGN PATENT DOCUMENTS

CN 1903122 A 1/2007
JP 2008-302221 12/2008
(Continued)

OTHER PUBLICATIONS

European Search Report completed Jul. 25, 2013 for corresponding Patent Application No. EP13167114.
(Continued)

*Primary Examiner* — May A Abouelela
(74) *Attorney, Agent, or Firm* — Dergosits & Noah LLP; Todd A. Noah (57) ABSTRACT

A medical apparatus, including a reference probe having a flexible insertion tube with a distal end for insertion into a body cavity, a pair of isolated electrodes fixedly attached to the distal end, and a position sensor fixedly located in the distal end. The apparatus also includes a supplementary probe having an electrode fixed thereto. The apparatus further includes a processor, configured to inject respective alternating currents into the pair of isolated electrodes so as to generate an electrical field therefrom, to measure a potential generated at the electrode of the supplementary probe in response to the electrical field, and to evaluate a location of the supplementary probe with respect to the reference probe in response to the measured potential and in response to a position of the distal end indicated by the position sensor.

8 Claims, 4 Drawing Sheets

(51) Int. Cl.
*A61B 34/20* (2016.01)
*A61B 5/053* (2006.01)
(52) U.S. Cl.
CPC .............. *A61B 5/6852* (2013.01); *A61B 5/72* (2013.01); *A61B 34/20* (2016.02); *A61B 2034/2053* (2016.02)
(58) Field of Classification Search
USPC ......... 600/300, 547, 377, 424, 373; 128/899
See application file for complete search history.

(56) References Cited

U.S. PATENT DOCUMENTS

| | | | |
|---|---|---|---|
| 5,899,860 | A | 5/1999 | Pfeiffer |
| 6,050,267 | A | 4/2000 | Nardella |
| 6,068,629 | A | 5/2000 | Haissaguerre et al. |
| 6,095,150 | A | 8/2000 | Panescu |
| 6,226,547 | B1 | 5/2001 | Lockhart |
| 6,456,864 | B1 | 9/2002 | Swanson |
| 6,574,498 | B1 | 6/2003 | Gilboa |
| 6,939,309 | B1 | 9/2005 | Beatty |
| 7,848,789 | B2 | 12/2010 | Govari |
| 8,417,313 | B2 | 4/2013 | Scharf et al. |
| 8,887,387 | B2* | 11/2014 | Pianca .................. H01R 43/00 29/847 |
| 9,675,795 | B2* | 6/2017 | Pianca ............... A61N 1/36182 |
| 2002/0068867 | A1* | 6/2002 | Ameling ................. A61B 5/06 600/424 |
| 2003/0018362 | A1 | 1/2003 | Fellows et al. |
| 2003/0060820 | A1 | 3/2003 | Maguire et al. |
| 2003/0139781 | A1 | 7/2003 | Zhu |
| 2009/0157136 | A1* | 6/2009 | Yang .................... A61B 5/0422 607/17 |
| 2009/0253976 | A1* | 10/2009 | Harlev ................. A61B 5/0422 600/374 |
| 2009/0312755 | A1 | 12/2009 | Thapliyal et al. |
| 2010/0137944 | A1 | 6/2010 | Zhu |
| 2010/0168558 | A1* | 7/2010 | Olson .................. A61B 5/0422 600/424 |
| 2010/0298690 | A1 | 11/2010 | Scharf |
| 2010/0324414 | A1* | 12/2010 | Harlev ................. A61B 5/0536 600/424 |
| 2011/0054551 | A1 | 3/2011 | Zhu et al. |
| 2011/0118590 | A1* | 5/2011 | Zhang ................... A61B 5/062 600/424 |
| 2011/0160593 | A1 | 6/2011 | Deno |
| 2011/0190625 | A1 | 8/2011 | Harlev |
| 2011/0282187 | A1* | 11/2011 | Harlev ................. A61B 5/0422 600/424 |
| 2012/0101369 | A1* | 4/2012 | Patil ..................... A61B 5/0538 600/424 |
| 2012/0143030 | A1* | 6/2012 | Harlev .................. A61B 5/053 600/375 |
| 2012/0150022 | A1 | 6/2012 | Bar-Tal |

FOREIGN PATENT DOCUMENTS

| | | |
|---|---|---|
| WO | WO 1994006349 A1 | 3/1994 |
| WO | WO 2012122517 A2 | 3/1994 |
| WO | 01/06917 A1 | 2/2001 |
| WO | WO 2008014629 A3 | 6/2008 |
| WO | WO 2009090547 A2 | 7/2009 |
| WO | WO 2012122517 A2 | 9/2012 |

OTHER PUBLICATIONS

Lee, K., Cardiac Ablation Catheter Guidance by Means of a Single Equivalent Moving Dipole Inverse Algorithm. PACE 2013; 00:1-12.
Scharf, G., Electrophysiology of Living Organs From First Principles. Physics.Bio-Ph, V1, pp. 1-14, Jun. 17, 2010.
Office Action for Chinese Patent Application No. 201310195042.0; dated Jul. 6, 2016.
Office Action for Australian Patent Application No. 2013205888; dated Oct. 13, 2016.
Office Action for Chinese Patent Application CN201310195042.0, dated Jan. 17, 2017.
Notice of Acceptance for Corresponding Australian Patent Application No. 2013205888 dated Nov. 28, 2016, 2 pages.
Notification of Reasons for Refusal in corresponding Japanese Patent Application No. 2013-107871, dated Jan. 17, 2017, pp. 1-4.
PCT Application Japanese Translation Publication 2000-516111, dated Mar. 21, 2017, pp. 1-11.
PCT Application Japanese Translation Publication 2010-514515, dated Mar. 21, 2017, pp. 1-33.
Written Opinion for European Patent Appl No. 13168660, dated Aug. 28, 2013.
Search Report for European Patent Appl No. 13168660, dated Aug. 28, 2013.
Search Report for Chinese Patent Appl No. 201310195042.0, dated Jun. 27, 2016.
Office Action for China Patent Application No. 201310195042.0, dated May 11, 2017.
Office Action for China Patent Application No. 201310195042.0, dated Nov. 28, 2017.

\* cited by examiner

POSITION SENSING USING ELECTRIC DIPOLE FIELDS

CROSS-REFERENCE TO RELATED APPLICATION

This application claims the benefit of U.S. Provisional Patent Application No. 61/650,631, filed May 23, 2012, which is incorporated herein by reference.

FIELD OF THE INVENTION

The present invention relates generally to position sensing, and specifically to position sensing by measurements of electric fields.

BACKGROUND OF THE INVENTION

A medical procedure within a body organ, such as the heart, typically uses one or more probes within the organ to perform various functions required by the procedure. The functions typically include operations such as ultrasonic or optical imaging, extraction of a biopsy sample, and/or performance of cryonic, ultrasonic or radio-frequency ablation. In the case of the heart the functions may also include measurement of electric potentials generated within the heart. Regardless of the functions, in all cases it is usually necessary to track the location and/or orientation of the operative portion of the probe, which is typically located at the distal end of the probe. Any method for improving the efficacy of such tracking would be beneficial.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides medical apparatus, including:
a reference probe, including:
a flexible insertion tube having a distal end for insertion into a body cavity;
a pair of isolated electrodes fixedly attached to the distal end; and
a position sensor fixedly located in the distal end;
a supplementary probe having an electrode fixed thereto; and
a processor, configured to inject respective alternating currents into the pair of isolated electrodes so as to generate an electrical field therefrom, to measure a potential generated at the electrode of the supplementary probe in response to the electrical field, and to evaluate a location of the supplementary probe with respect to the reference probe in response to the measured potential and in response to a position of the distal end indicated by the position sensor.

In a disclosed embodiment the pair of isolated electrodes includes three pairs of mutually isolated electrodes. Typically, the three pairs of mutually isolated electrodes respectively define three axes which are mutually orthogonal. The processor may be configured to respectively inject three sets of respective alternating currents into the three pairs of mutually isolated electrodes.

In a further disclosed embodiment the position sensor includes at least one coil, and the processor is configured to measure the position of the distal end, as a distal end location and a distal end orientation, using electrical signals generated in the at least one coil in response to a magnetic field.

In a yet further disclosed embodiment the supplementary probe has a further electrode fixed thereto, and the processor is configured to measure a further potential generated at the further electrode in response to the electrical field, and to evaluate a further location of the further electrode with respect to the reference probe in response to the measured further potential and in response to the position of the distal end indicated by the position sensor, and to evaluate an orientation of the supplementary probe in response to the location of the supplementary probe and the further location of the further electrode.

In an alternative embodiment the apparatus includes:
an alternate reference probe, including:
an alternate flexible insertion tube having an alternate distal end for insertion into the body cavity; and
an alternate pair of isolated electrodes fixedly attached to the alternate distal end,
wherein the processor is configured to measure further potentials generated at the alternate pair of isolated electrodes of the supplementary probe in response to the electrical field, and to evaluate an alternate reference probe location and an alternate reference probe orientation in response to the measured further potentials.

Typically, the processor is configured to inject respective further alternating currents into the alternate pair of isolated electrodes so as to generate a further electrical field therefrom. The processor may be configured to measure a further potential generated at the electrode of the supplementary probe in response to the further electrical field, and to further evaluate the location of the supplementary probe in response to the measured further potential, the alternate reference probe location and the alternate reference probe orientation. The apparatus may include a further supplementary probe having a further electrode outside the electrical field and within the further electrical field, wherein the processor is configured to measure a further potential generated at the further electrode of the further supplementary probe in response to the further electrical field, and to evaluate a further supplementary probe location in response to the measured further potential, the alternate reference probe location and the alternate reference probe orientation.

There is further provided, according to an embodiment of the present invention, a method, including:
providing a reference probe, including a flexible insertion tube having a distal end for insertion into a body cavity;
fixedly attaching a pair of isolated electrodes to the distal end; and
fixedly locating a position sensor in the distal end;
fixing an electrode to a supplementary probe;
injecting respective alternating currents into the pair of isolated electrodes so as to generate an electrical field therefrom;
measuring a potential generated at the electrode of the supplementary probe in response to the electrical field; and
evaluating a location of the supplementary probe with respect to the reference probe in response to the measured potential and in response to a position of the distal end indicated by the position sensor.

The present disclosure will be more fully understood from the following detailed description of the embodiments thereof, taken together with the drawings, in which:

DETAILED DESCRIPTION OF EMBODIMENTS

Overview

An embodiment of the present invention comprises medical apparatus which is configured to act as a tracking system for a catheter, also herein termed a supplementary probe, within a body cavity. The body cavity is typically the heart, although catheters within other body cavities, such as the chest, may also be tracked.

The apparatus comprises a reference probe which is inserted into the body cavity. The reference probe comprises a flexible insertion tube having a distal end, and the reference probe distal end is inserted into the body cavity. At least one pair, and typically three pairs, of isolated electrodes are fixedly attached to the reference probe distal end, and a position sensor is located in the distal end.

A processor injects respective alternating currents into each pair of electrodes, and the injected currents generate electric fields, which typically approximate to dipole fields.

The supplementary probe to be tracked has an electrode fixed to the probe, and in response to the electric fields the electrode generates a potential. The processor measures the potential, and from the measured potential and a position of the reference probe as indicated by the position sensor, is able to evaluate a location of the supplementary probe.

The apparatus may be used to track multiple supplementary probes simultaneously. By using dipole fields to track the supplementary probes, the probes may be tracked to sub-mm accuracy.

System Description

Figure 1:
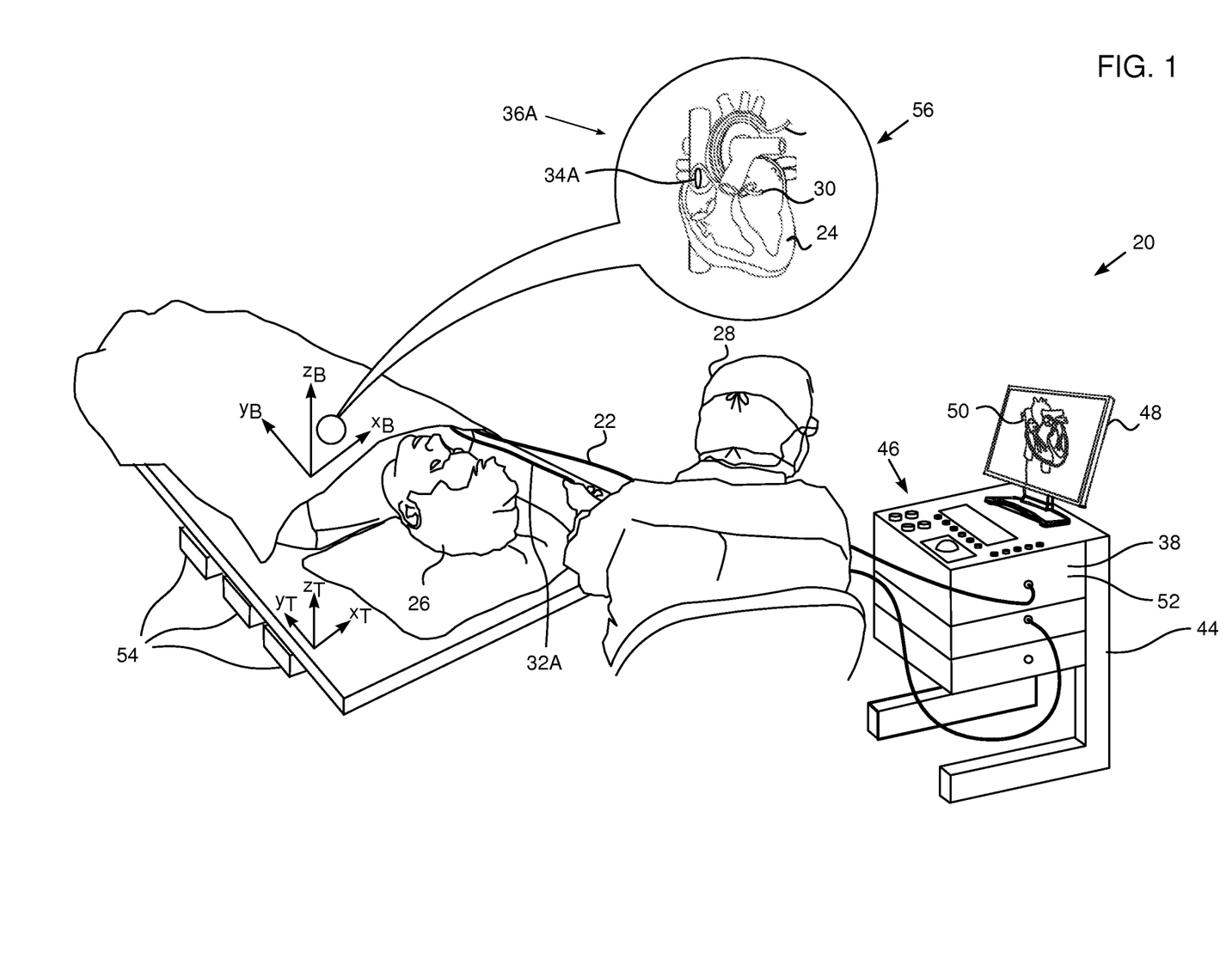
FIG. 1 is a schematic illustration of a catheter tracking system, according to an embodiment of the present invention.

Reference is now made to FIG. 1, which is a schematic illustration of a catheter tracking system 20, according to an embodiment of the present invention. In order to perform its tracking, system 20 uses a reference probe 22, and for simplicity and clarity, the following description assumes by way of example that system 20 operates while a medical procedure is performed on a heart 24, herein assumed to comprise a human heart, using the probe. System 20 typically includes facilities used during the medical procedure, such as a facility for ablating one or more regions of heart 24.

Reference probe 22, also referred to herein as reference catheter 22, comprises a flexible insertion tube which is inserted into the body of a subject 26 during the medical procedure. A user 28 of system 20 performs the medical procedure, and in the description herein user 28 is assumed, by way of example, to be a medical professional. A distal end 30 of the reference probe is assumed to be positioned within heart 24, and the structure of the reference probe distal end is described below, with reference to FIGS. 2A and 2B.

In addition to reference probe 22, professional 28 also uses probes 32A, 32B, . . . collectively referred to herein as probes 32, during the medical procedure. Probes 32, also referred to herein as supplementary probes, have respective distal ends 34A, 34B, . . . collectively referred to herein as distal ends 34. For simplicity only supplementary probe 32A and its distal end 34A are shown in FIG. 1. Supplementary probes 32 are generally similar, but may vary in shape and structure, and may be used for a variety of purposes, such as ablation of heart 24, and/or investigations of electro-potentials generated by the heart. However, in the present disclosure, respective electrodes 36A, 36B, . . . collectively referred to as electrodes 36, are assumed to be attached to distal ends 34A, 34B . . . . As described below, signals generated at electrodes 36 are used to measure locations of respective distal ends 34.

Typically there is more than one electrode attached to each distal end 34; as necessary, such electrodes are differentiated by appending a numeral to the electrode identifier. For example, electrodes 36A1, 36A2, . . . may be attached to distal end 34A of probe 32A.

System 20 may be controlled by a system processor 38 which may be realized as a general purpose computer. Processor 38 may be mounted in a console 44, comprising operating controls 46 that typically include a keypad and a pointing device such as a mouse or trackball that professional 28 uses to interact with the processor. Results of the operations performed by processor 38 are provided to the professional on a screen 48 connected to the processor. The results include the locations of distal ends 34, and the locations may be displayed graphically on an image 50 of heart 24 that is generated on screen 48. Alternatively or additionally the locations of distal ends 34 may be displayed numerically, or in any other convenient form, on screen 48. Screen 48 typically also presents a graphic user interface to the professional. Professional 28 is able to use controls 46 to input values of parameters used by processor 38 in the operation of system 20.

Processor 38 uses computer software, including a reference probe tracker module 52, to operate system 20. The software may be downloaded to processor 38 in electronic form, over a network, for example, or it may, alternatively or additionally, be provided and/or stored on non-transitory tangible computer-readable media, such as magnetic, optical, or electronic memory.

Probe tracker module 52 tracks distal end 30 while the probe is within subject 26. The tracker module typically tracks both the location and the orientation of the distal end of the reference probe, within the heart of subject 26. In some embodiments module 52 tracks other sections of the probe. While the tracker module may use any method for tracking probes known in the art, using an appropriate position sensor, in the present description for clarity and simplicity module 52 is assumed to comprise a magnetic tracker, such as the Carto® system produced by Biosense Webster, of Diamond Bar, Calif. Module 52 operates magnetic field transmitters 54 in the vicinity of subject 26, so that magnetic fields from the transmitters interact with one or more tracking coils 56, located in distal end 30, forming a distal end position sensor. The one or more tracking coils are also referred to herein as distal end position sensor 56.

The coils interacting with the magnetic fields generate signals which are transmitted to the module, and the module analyzes the signals to determine a location and orientation of distal end 30. Alternatively or additionally, tracker module 52 may track the distal end of probe 22 by measuring impedances between one or more of electrodes on the reference probe distal end and electrodes on the skin of subject 26. The Carto3® system produced by Biosense Webster uses both magnetic field transmitters and impedance measurements for tracking. U.S. Pat. No. 7,848,789, to Govari et al., whose disclosure is incorporated herein by reference, describes using both magnetic fields and impedance measurements for probe tracking. Further alternatively or additionally, module 52 may determine the location and orientation of distal end 30 using any other means known in the art, such as by analysis of fluoroscopic or ultrasonic images.

Transmitters 54 are fixed, and define a transmitter frame of reference in terms of a first set of orthogonal axes $x_T$, $y_T$, $z_T$ which are fixed with respect to the transmitters. However, while the signals derived from coils 56 provide coordinates of the location and orientation of distal end 30 with respect to the transmitter frame of reference, professional 28 typically requires knowledge of the location and orientation of the distal end with respect to subject 26.

In order to provide this latter location and orientation, a set of patient position sensors are attached to the skin of subject 26. Typically the patient position sensors are attached to known locations on the back of the subject. Module 50 receives signals from the sensors, and uses the signals to define a body coordinate frame of reference in terms of a second set of body coordinate orthogonal axes $x_B$, $y_B$, $z_B$ which are fixed with respect to subject 26. During the procedure performed by professional 28, processor 38 registers the two frames of reference, and so is able to generate the location and orientation of reference probe distal end 30 with respect to the subject. U.S. Patent Application 2012/0150022, to Bar-Tal et al., which is incorporated herein by reference, describes a body coordinate frame of reference system and registration of the system to a coordinate system based on magnetic transmitters.

Figure 2A:
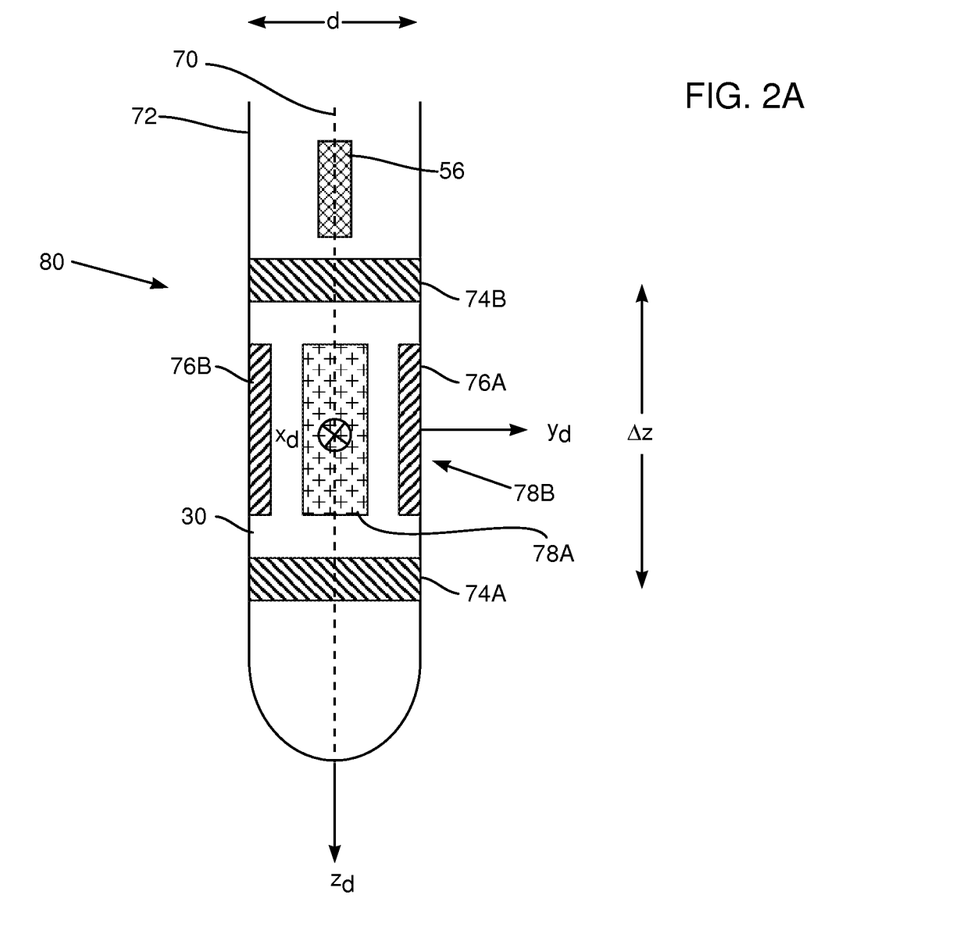
FIGS. 2A and 2B are schematic diagrams illustrating cross-sections of a distal end of a reference probe used in the system, according to an embodiment of the present invention.
Figure 2B:
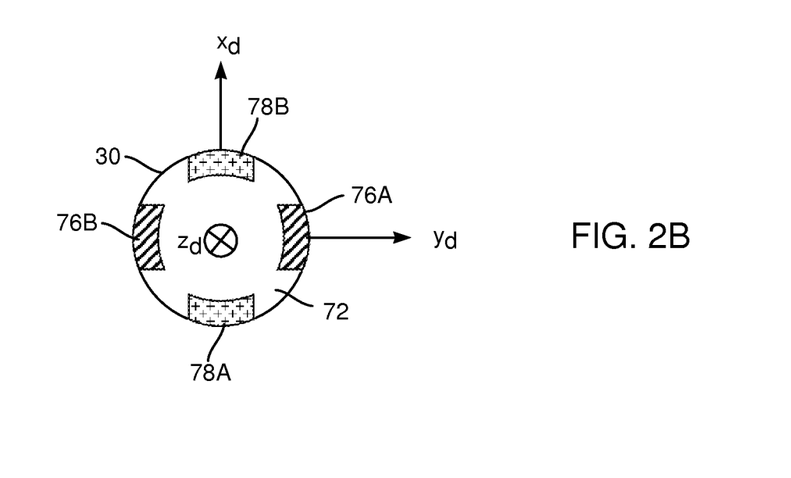

FIGS. 2A and 2B are schematic diagrams illustrating cross-sections of distal end 30 of the reference probe, according to an embodiment of the present invention.

Reference probe 22 is typically circular in cross-section, having a diameter d and having an axis of symmetry 70. For clarity, distal end 30 of the probe is assumed to be constructed with reference to a set of orthogonal $x_d y_d z_d$ axes, with axis 70 corresponding to the $z_d$ axis. FIG. 2A shows a first cross-section, taken with axis 70 lying in the plane of the cross-section (corresponding to the plane of the paper). The plane of the cross-section is assumed to define a $y_d$ axis that is orthogonal to the $z_d$ axis and in the plane of the cross-section, and an $x_d$ axis is perpendicular to the plane of the cross-section. FIG. 2B shows a second cross-section which is taken in the $x_d y_d$ plane.

Position sensor 56, comprising one or more tracking coils, is located in distal end 30. In addition, three pairs of electrodes are formed at distal end 30, typically on an insulating surface 72 of the distal end. Each electrode is electrically isolated from the other electrodes, and the pairs of electrodes are configured to have respective axes orthogonal to each other.

Thus, a first pair of electrodes 74A, 74B is formed as ring electrodes on surface 72, the electrodes having axis 70 as a common axis, and being separated from each other by a distance $\Delta z$. A second pair of electrodes 76A, 76B is formed on surface 72 at opposite ends of a $y_d$ axis diameter of the distal end, so that the electrodes are separated by distance d. A third pair of electrodes 78A, 78B is formed on surface 72 at opposite ends of an x axis diameter of the distal end, so that the electrodes are also separated by distance d. Typically, although not necessarily, electrodes 76A, 76B, 78A, and 78B have the same shape, and are herein assumed by way of example to be approximately rectangular. Electrodes 74A, 74B, 76A, 76B, 78A, and 78B are also collectively referred to herein as electrodes 80. However, there is no necessity that the shapes of electrodes 80, even of a pair, be the same or that they be rectangular, and the electrodes may have any convenient configuration. Typically, each pair of electrodes 80 has a center of symmetry. Usually, the centers of symmetry of the different pairs are at a common point, herein assumed to correspond to an origin of the $x_d y_d z_d$ frame. The origin of the frame is a point on axis 70.

For clarity, in FIG. 2A position sensor 56 is shown separated from electrodes 80. However, typically the sensor is located close to the origin of the $x_d y_d z_d$ frame.

The six electrodes 80 are connected by conducting wires to and operated by processor 38. In addition, position sensor 56 is also connected to the processor. For simplicity the connections are not shown in the figures, but the processor uses the connections to operate the electrodes and to use the sensor, as described in more detail with reference to FIG. 3.

Figure 3:
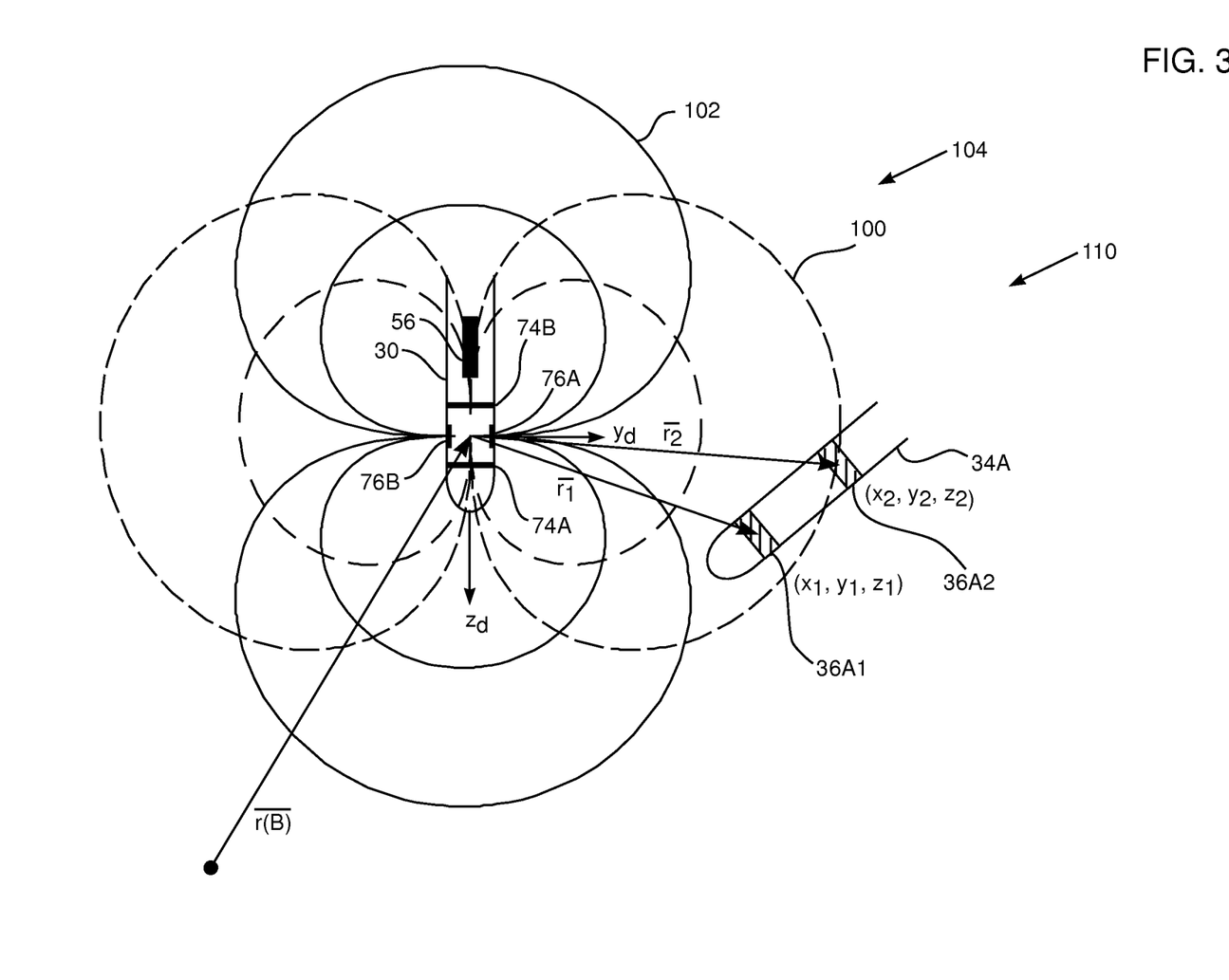
FIG. 3 is a schematic diagram illustrating operation of the catheter tracking system, according to an embodiment of the present invention.

FIG. 3 is a schematic diagram illustrating operation of catheter tracking system 20, according to an embodiment of the present invention. As explained below, processor 38 is able to track the locations of electrodes attached to distal ends of supplementary probes when the electrodes are in the vicinity of distal end 30 of the reference catheter. For simplicity, only one supplementary probe distal end 34A, having two attached electrodes 36A1, 36A2, is shown in FIG. 3.

Processor 38 uses position sensor 56 to evaluate the location and orientation of reference probe distal end 30. The processor operates magnetic field generators 54, and measures electrical signals induced by the generated magnetic fields in the coils of the sensor. The processor calculates the location and orientation of the reference probe distal end 30 from the induced electrical signals.

By operating position sensor 56, processor 38 determines a location vector $\overline{r(B)} \equiv (x,y,z)$ of distal end 30 with respect to the body coordinate frame of reference referred to above, i.e., with reference to axes $x_B$, $y_B$, $z_B$. In addition, the processor may use sensor 56 to find an orientation vector $\varphi(B)$, corresponding the $z_d$ axis direction, of the distal end, as measured in the body frame of reference.

Processor 38 uses tracker module 52 to inject alternating electric currents into the pairs of electrodes 80, so that each of the three pairs of electrodes acts approximately as an electric dipole radiator having a respective dipole moment and radiating a respective alternating electric field. Thus, electrodes 74A, 74B act as a first dipole having a first dipole moment directed along the $z_d$ axis. Similarly, electrodes 76A, 76B act as a second dipole having a second dipole moment directed along the $y_d$ axis, and electrodes 78A, 78B (FIGS. 2A, 2B) act as a third dipole having a third dipole moment directed along the $x_d$ axis. For each dipole, the magnitude of the respective dipole moment is approximately proportional to the current injected into the respective electrodes forming the dipole; the magnitude is also a function of the separation of the electrodes forming the dipole.

Typically processor 38 multiplexes the alternating electric current injection, for instance by time and/or frequency multiplexing, so that the processor is able to distinguish signals generated by the different pairs.

A field 100 from electrodes 74A and 74B is represented schematically as broken lines, and a field 102 from electrodes 76A and 76B is represented schematically as solid lines. A field 104 from electrodes 78A and 78B, the lines of which are not shown in FIG. 3 for clarity, is typically substantially similar to field 102, but is rotated by 90° about the $z_d$ axis. Fields 100, 102, and 104 are collectively referred to herein as fields 110.

To a first approximation fields 110 may be considered to be dipole fields, and are also referred to herein as dipole fields 110. Methods that may be invoked to accommodate the case when the dipole field approximation is not adequate are described below.

The following analysis derives an expression for the potentials generated by the dipole radiators of the reference probe. The alternating current injected by module 52 into pair of electrodes 78A, 78B on the $x_d$ axis (also referred to as the x electrodes) is assumed to be $+I_x$, $-I_x$. Similarly, the alternating current injected into electrodes 76A, 76B on the $y_d$ axis (the y electrodes) is assumed to be $+I_y$, $-I_y$ and the current injected into electrodes 74A, 74B on the $z_d$ axis (the z electrodes) is assumed to be $+I_z$, $-I_z$. The currents cause the respective pairs of electrodes to behave as current dipoles.

From Coulomb's law, a point charge q generates a potential V at a distance r from the charge given by equation (1):

$$V = \frac{q}{4\pi\varepsilon_0 r} \quad (1)$$

For a current source I operating in a medium having a conductivity σ, then equation (1) may be rewritten:

$$V = \frac{I}{4\pi\sigma r} \quad (2)$$

Assuming that electrode 36A1 is at a location $\overline{r_1} \equiv (x_1, y_1, z_1)$ in the reference probe frame of reference, then from equation (2) the potential generated by the current dipole formed by x electrodes 78A, 78B is given by:

$$V_x = \frac{I_x}{4\pi\sigma}\left(\frac{1}{\sqrt{\left(-\frac{d_x}{2}+x_1\right)^2+y_1^2+z_1^2}} - \frac{1}{\sqrt{\left(\frac{d_x}{2}+x_1\right)^2+y_1^2+z_1^2}}\right) \equiv A_x \quad (3)$$

where $d_x$ is the separation of the x electrodes.

Equations (4) and (5) respectively give the potentials generated by the current dipole formed by the y electrodes 76A, 76B, and by the current dipole formed by the z electrodes 74A, 74B:

$$V_y = \frac{I_y}{4\pi\sigma}\left(\frac{1}{\sqrt{x_1^2+\left(-\frac{d_y}{2}+y_1\right)^2+z_1^2}} - \frac{1}{\sqrt{x_1^2+\left(\frac{d_y}{2}+y_1\right)^2+z_1^2}}\right) \equiv A_y \quad (4)$$

$$V_z = \frac{I_z}{4\pi\sigma}\left(\frac{1}{\sqrt{x_1^2+y_1^2+\left(-\frac{d_z}{2}+z_1\right)^2}} - \frac{1}{\sqrt{x_1^2+y_1^2+\left(\frac{d_z}{2}+z_1\right)^2}}\right) \equiv A_z \quad (5)$$

where $d_y$, $d_z$ are the separation of the y and z electrodes respectively. (In the typical case of a circular probe, $d_y=d_x$.) The expressions $A_x$, $A_y$, and $A_z$ are referred to below.

To measure the location $\overline{r_1}$ of electrode 36A1, module 52 injects currents $\pm I_x$, $\pm I_y$, and $\pm I_z$ into the x, y and z electrodes, and measures potentials $V_x$, $V_y$, and $V_z$. Processor 38 uses the measured values of $V_x$, $V_y$, $V_z$, the values of $I_x$, $I_y$, and $I_z$, and a value of conductivity σ, to solve the three equations (3), (4) and (5) for values of $x_1$, $y_1$, and $z_1$. Processor 38 typically applies the known geometry of the cavity wherein the reference and supplementary probes are located to eliminate possible aliased values for $x_1$, $y_1$, and $z_1$. Other methods for eliminating incorrect aliased locations are described below.

Equations (3) (4) and (5) are based on fields 110 behaving as fields from ideal dipoles. The equations may be modified, by addition of higher-order spherical harmonics, for example, to account for variations from the ideal behavior. In addition, reference probe 22 may be calibrated and/or equations (3) (4) and (5) may be modified to account for the non-zero distance between pairs of electrodes 80 and inhomogeneities of a volume or cavity within which system 20 is operating. The calibration may include determination of an effective value for conductivity σ, by processor 38 injecting a known voltage across two of electrodes 80, and the processor measuring the current generated by the voltage.

Once processor 38 has determined location $\overline{r_1}$ of electrode 36A1 in the reference probe frame of reference, the processor may calculate the location of the electrode in the body frame of reference using the location vector of position sensor 56, $\overline{r(B)}$. Thus, a location $\overline{R_1}$ of electrode 36A1 in the body frame of reference is given by equation (6):

$$\overline{R_1} = \overline{r(B)} + \overline{r_1} \quad (6)$$

Processor 38 may apply a similar process to that described above (for determining the location of electrode 36A1 and thus of distal end 34A) to evaluate the location of other electrodes and their associated distal ends.

For a distal end having more than one attached electrode, the orientation of the distal end, as well as its location, may also be found. For example, if distal end 34A has a second electrode 36A2, then processor 38 may determine a location $\overline{r_2}$ of electrode 36A2 in the reference probe frame of reference. An orientation $\overline{\Psi_1}$ of the distal end is given by equation (7):

$$\overline{\Psi_1} = \overline{r_1} - \overline{r_2} \quad (7)$$

Typically, for a distal end having more than one attached electrode, processor 38 may make a more accurate determination of the distal end location by averaging locations of the attached electrodes.

Equations (3), (4) and (5) may be written (using the definitions of $A_x$, $A_y$, and $A_z$ in the equations) in matrix form as:

$$\begin{pmatrix} V_x \\ V_y \\ V_z \end{pmatrix} = \begin{pmatrix} A_x \\ A_y \\ V_z \end{pmatrix} \quad (8)$$

From equation (8) a change in location of electrode 36A1 by a small distance (dx,dy,dz) at a location (x,y,z) will generate a potential change ($dV_x,dV_y,dV_z$) at the electrode given by:

$$\begin{pmatrix} dV_x \\ dV_y \\ dV_z \end{pmatrix} = J \begin{pmatrix} dx \\ dy \\ dz \end{pmatrix} \quad (9)$$

Where J is the Jacobian of $$\begin{pmatrix} A_x \\ A_y \\ V_z \end{pmatrix}.$$

An expression for J, is given by equation (10) below. Equation (10) assumes for simplicity that $d_1=d_2=d_3=d$, (the spacing of pairs of electrodes) and that $I_x=I_y=I_z=I$. Equation (10) also assumes that a distance r to location (x, y, z), is given by $r^2=x^2+y^2+z^2$, replaces ($x_1, y_1, z_1$) by (x, y, z), and assumes that d (the electrode spacing) is small compared to r.

$$J = \begin{pmatrix} \frac{dI}{4\pi r^5 \sigma}(-2x^2+y^2+z^2) & \frac{dI}{4\pi r^5 \sigma}(-3dxy) & \frac{dI}{4\pi r^5 \sigma}(-3dxz) \\ \frac{dI}{4\pi r^5 \sigma}(-3dxy) & \frac{dI}{4\pi r^5 \sigma}(x^2-2y^2+z^2) & \frac{dI}{4\pi r^5 \sigma}(-3dyz) \\ \frac{dI}{4\pi r^5 \sigma}(-3dxz) & \frac{dI}{4\pi r^5 \sigma}(-3dyz) & \frac{dI}{4\pi r^5 \sigma}(x^2+y^2-2z^2) \end{pmatrix} \quad (10)$$

The expression for the Jacobian given in equation (10) assumes that fields 80 are those of ideal dipoles. The expression may be modified to account for variations from ideal behavior, by methods that will be apparent to those having ordinary skill in the art. Such modifications include, for example, using higher-order spherical harmonics.

The dipole approximation given by equations (3), (4) and (5) gives good results for supplementary catheters 36 that are more than approximately 5 mm from reference catheter 22. A typical working distance, measured from the reference catheter, for supplementary catheters 36 is up to approximately 10 cm. An operating volume for reference catheter 22, i.e., the volume wherein the electric fields from the electrodes are effective, is typically approximately equal to a sphere radius 10 cm.

In an embodiment, a frequency of the alternating currents injected into electrodes 80 is typically of the order of 100 kHz, and the magnitude of the current injected is typically of the order of 10 mA, although frequencies and currents (such as in the example below) different from these values are possible.

As a numerical example, for reference catheter 30 having a diameter of approximately 2 mm, so that x and y pairs of electrodes are separated by approximately 2 mm, and assuming the z axis electrodes are also separated by approximately 2 mm, assume that d=2 mm. The numerical example makes the following further assumptions:

electrode 36A1 is 5 cm from reference probe distal end 30;
the conductivity σ is 0.5 S/m; and
I=1 mA, where $I_x=I_y=I_z=I$.

Applying the above assumptions, equations (9) and (10) gives sensitivities of approximately (−5.1, 2.5, 2.5) [μV/mm] for each of the directions (x,y,z) at a point (5, 0, 0) on the x axis of the reference probe. Similar values for the sensitivity apply at other points that are 5 cm from the reference probe. These sensitivities enable sub-mm measurements of a supplementary probe location in a typical system.

The description above has assumed that the pairs of electrodes 80 have a common center. It will be understood that this is not a necessary condition for embodiments of the present invention to operate, so that, in general, each pair of electrodes may have a center that is not coincident with any other center.

While the description above has assumed three pairs of electrodes attached to the distal end of the reference catheter it will be understood that locations of supplementary probes may be determined using fewer than three pairs. For example, using only one pair, while the fields generated from the electrodes may not give a unique location for a supplementary probe in a cavity, other factors, such as the dimensions of the cavity, may be sufficient to provide a unique value for the location. The scope of the present invention is thus assumed to comprise fewer than three pairs of electrodes attached to the distal end of the reference catheter.

Alternatively, there may be more than three pairs of electrodes attached to the reference catheter. Having more than three pairs generates redundancy in the measurements, and the redundancy may be used to increase the accuracy of the measured locations of the supplementary probe distal ends. Alternatively or additionally, providing more than three pairs of electrodes may eliminate incorrect aliased locations that may be generated if only three pairs of electrodes are used.

Figure 4:
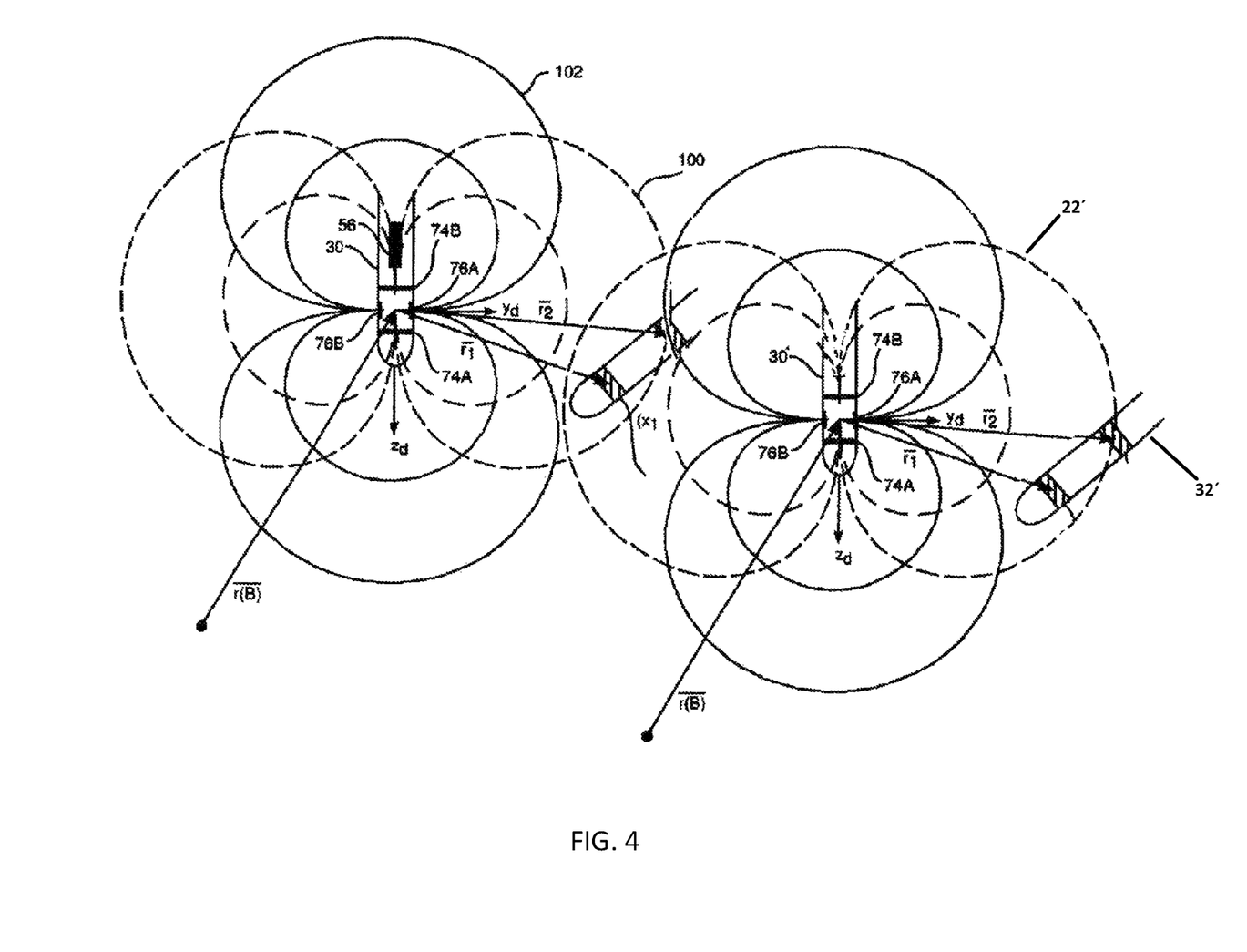
FIG. 4 is a schematic diagram illustrating operation of the catheter tracking system, according to an embodiment of the present invention.

Further alternatively, as shown in FIG. 4, more than one reference probe 22' may be used in system 20, processor 38 injecting respective alternating currents into each of the pairs of electrode of each further reference probe. Using multiple reference probes increases the overall volume wherein system 20 is able to measure locations of supplementary probes. In addition, where the individual operating volumes of the reference probes overlap, processor 38 is able to use the multiple values for a given supplementary probe location to increase the accuracy of the location, and/or to eliminate incorrect aliased locations. Furthermore, only one of the multiple reference probes may need to have a position sensor (position sensor 56), since the locations and orientations of the other reference probes may be measured with respect to that reference probe. Using the measured locations and orientations of the other reference probes, the processor may, alternatively or additionally, be able to evaluate the locations of further supplementary probes 32' that may be outside the operating volume, i.e., beyond the effective electrical field, of the reference probe having the position sensor.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A medical apparatus, comprising: a reference probe, comprising:
   a flexible insertion tube having a circumferential surface extending along a longitudinal axis, a distal end configured to be inserted a body cavity, the distal end having a distal tip;
   at least three pairs of mutually isolated electrodes fixedly attached linearly along the circumferential surface of the flexible insertion tube:
   i] a first pair of the at least three pairs of mutually isolated electrodes being a pair of ring electrodes proximal the distal tip and separated by a first fixed distance along the longitudinal axis to be a first dipole having a dipole moment directed along the longitudinal axis,
   ii] a second pair of the at least three pairs of mutually isolated electrodes being radially offset from each other by 180° along a second pair axis perpendicular to the longitudinal axis to be a second dipole having a dipole moment directed along the second pair axis, and
   iii] a third pair of the at least three pairs of mutually isolated electrodes being radially offset from each other by 180° along a third pair axis perpendicular to the longitudinal axis and orthogonal to the second pair axis to be a third dipole having a dipole moment directed along the third pair axis, the second pair of mutually isolated electrodes and the third pair of mutually isolated electrodes being positioned directly on the surface of the distal end between the first pair of mutually isolated ring electrodes, wherein each electrode of each of the at least three pairs of mutually isolated electrodes comprising source electrodes for generating an electrical field; and
   a position sensor fixedly located in the distal end; a supplementary probe having an electrode fixed thereto; and
   a processor, configured to inject respective alternating currents into at least one pair of the at least three pairs of mutually isolated electrodes to generate the electrical field therefrom, to measure a potential generated at the electrode of the supplementary probe in response to the electrical field, and to determine a location of the electrode on the supplementary probe with respect to a reference probe frame of reference and to then calculate the location of the electrode on the supplementary probe in the frame of reference using a location vector relating to a position of the position sensor.

2. The apparatus according to claim 1, wherein the processor is configured to respectively inject three sets of respective alternating currents into the three pairs of mutually isolated electrodes.

3. The apparatus according to claim 1, wherein the position sensor comprises at least one coil, and wherein the processor is configured to measure the position of the distal end, as a distal end location and a distal end orientation, using electrical signals generated in the at least one coil in response to a magnetic field.

4. The apparatus according to claim 1, wherein the supplementary probe has a further electrode fixed thereto, and wherein the processor is configured to measure a further potential generated at the further electrode in response to the electrical field, and to evaluate a further location of the further electrode with respect to the reference probe in response to the measured further potential and in response to the position of the distal end indicated by the position sensor, and to evaluate an orientation of the supplementary probe in response to the location of the supplementary probe and the further location of the further electrode.

5. The apparatus according to claim 1, and comprising: a second reference probe, comprising:
   a second flexible insertion tube having a second distal end configured to be inserted into the body cavity; and
   a second pair of isolated electrodes fixedly attached to the second distal end, wherein the processor is configured to measure further potentials generated at the alternate pair of isolated electrodes of the supplementary probe in response to the electrical field, and to evaluate an alternate reference probe location and an alternate reference probe orientation in response to the measured further potentials.

6. The apparatus according to claim 5, wherein the processor is configured to inject respective further alternating currents into the second pair of isolated electrodes to generate a further electrical field therefrom.

7. The apparatus according to claim 6, wherein the processor is configured to measure a further potential generated at the electrode of the supplementary probe in response to the further electrical field, and to further evaluate the location of the supplementary probe in response to the measured further potential, the second reference probe location and the second reference probe orientation.

8. The apparatus according to claim 6, and comprising a further supplementary probe having a further electrode outside the electrical field and within the further electrical field, wherein the processor is configured to measure a further potential generated at the further electrode of the further supplementary probe in response to the further electrical field, and to evaluate a further supplementary probe location in response to the measured further potential, the second reference probe location and the second reference probe orientation.

* * * * *